United States Patent
Jansson et al.

(10) Patent No.: US 9,138,380 B2
(45) Date of Patent: Sep. 22, 2015

(54) PREPARATION OF MEDICAL SOLUTIONS FROM POWDERY MATERIAL

(75) Inventors: Olof Jansson, Vellinge (SE); Lennart Jonsson, Bjarred (SE); Torbjorn Linden, Hasslo (SE); Jan Sternby, Lund (SE); Ragnar Tryggvason, Loddekopinge (SE); Anders Wieslander, Lund (SE)

(73) Assignee: Gambro Lundia AB, Lund (SE)

( * ) Notice: Subject to any disclaimer, the term of this patent is extended or adjusted under 35 U.S.C. 154(b) by 230 days.

(21) Appl. No.: 13/805,557

(22) PCT Filed: Jun. 20, 2011

(86) PCT No.: PCT/EP2011/060255
§ 371 (c)(1),
(2), (4) Date: Apr. 10, 2013

(87) PCT Pub. No.: WO2011/161064
PCT Pub. Date: Dec. 29, 2011

(65) Prior Publication Data
US 2013/0190681 A1    Jul. 25, 2013

Related U.S. Application Data

(60) Provisional application No. 61/358,009, filed on Jun. 24, 2010.

(30) Foreign Application Priority Data

Jun. 23, 2010    (SE) ........................... 1050684

(51) Int. Cl.
*A61J 1/20*    (2006.01)
*A61M 1/28*    (2006.01)
(Continued)

(52) U.S. Cl.
CPC *A61J 1/20* (2013.01); *A61J 1/2093* (2013.01); *A61M 1/167* (2014.02); *A61M 1/1656* (2013.01);
(Continued)

(58) Field of Classification Search
CPC ........... B65D 81/3266; B65D 81/3294; B65D 1/095; B65D 75/30; B65D 75/305; B65D 75/32; B65D 75/321; B65D 75/323; B65D 75/325; B65D 75/327; B65D 75/34; B65D 75/36; B65D 75/367; B65D 75/5855; B65D 81/3261; B65D 25/00; B65D 81/2007; B65D 81/2023; B65D 81/2038; B65D 65/406; B65D 2231/002; F16K 15/142; A61J 2001/2024; A61J 1/2093
See application file for complete search history.

(56) References Cited

U.S. PATENT DOCUMENTS 3,722,833 A      3/1973   Inoue et al.
4,237,935 A  *  12/1980   Delmonte et al. ............ 137/860
(Continued)

FOREIGN PATENT DOCUMENTS

EP      0 456 220 A2    11/1991
JP      7300161          11/1995
(Continued)

OTHER PUBLICATIONS

Google machine translation WO 2004080369 A1, Apr. 22, 2015.*
(Continued)

*Primary Examiner* — Adam Marcetich
(74) *Attorney, Agent, or Firm* — K&L Gates LLP

(57) ABSTRACT

A package has a transport/storage state for storing powdery material which is to be mixed with a solvent to form a medical solution. The package includes a compartment which is at least partially defined by two opposing wall portions, and a connector. In the transport/storage state, the compartment contains the powdery material in the form of at least two distinct sets of powdery material of different compositions, where the opposing wall portions are brought into engagement with the powdery material so as to immobilize the sets of powdery material. When used for preparation of the medical solution, a fluid is selectively admitted into the package via the connector so as to expand the compartment and enable mixing of the sets of powdery material with the solvent in the compartment.

37 Claims, 7 Drawing Sheets

(51) Int. Cl.
*B65D 81/20* (2006.01)
*A61M 1/16* (2006.01)
*B65D 81/18* (2006.01)
*B65D 30/24* (2006.01)

(52) U.S. Cl.
CPC ............ *A61M 1/1666* (2014.02); *A61M 1/287* (2013.01); *B65D 31/14* (2013.01); *B65D 81/18* (2013.01); *B65D 81/20* (2013.01); *B65D 81/2007* (2013.01); *B65D 81/2023* (2013.01); *B65D 81/2046* (2013.01)

(56) References Cited

U.S. PATENT DOCUMENTS

| | | | | |
|---|---|---|---|---|
| 4,549,565 | A * | 10/1985 | Short, III | 137/71 |
| 4,664,891 | A | 5/1987 | Cosentino et al. | |
| 4,684,025 | A * | 8/1987 | Copland et al. | 206/484 |
| 5,385,564 | A * | 1/1995 | Slater et al. | 604/416 |
| 6,605,214 | B1 | 8/2003 | Taylor | |
| 2002/0141664 | A1 | 10/2002 | Matsuda et al. | |
| 2003/0111492 | A1 | 6/2003 | Gupta et al. | |
| 2003/0114333 | A1 * | 6/2003 | Somerville-Roberts et al. | 510/297 |
| 2003/0124329 | A1 * | 7/2003 | Fujio et al. | 428/216 |
| 2004/0065679 | A1 | 4/2004 | Peuker et al. | |
| 2004/0243094 | A1 * | 12/2004 | Dumon D'Ayot et al. | 604/410 |
| 2005/0031509 | A1 | 2/2005 | D'Ayot et al. | |
| 2006/0115395 | A1 | 6/2006 | Taylor | |
| 2006/0127540 | A1 * | 6/2006 | Keckeis | 426/120 |
| 2006/0196784 | A1 * | 9/2006 | Murray | 206/219 |
| 2007/0144923 | A1 | 6/2007 | Houwaert et al. | |
| 2008/0149668 | A1 * | 6/2008 | Johnson et al. | 222/107 |
| 2010/0014789 | A1 * | 1/2010 | Binger et al. | 383/109 |
| 2010/0039882 | A1 | 2/2010 | Suchan et al. | |
| 2010/0069817 | A1 | 3/2010 | Falkvall et al. | |
| 2010/0101612 | A1 * | 4/2010 | Wiedemann et al. | 134/25.2 |
| 2011/0210143 | A1 * | 9/2011 | Jones | 222/1 |

FOREIGN PATENT DOCUMENTS

| | | | | |
|---|---|---|---|---|
| JP | 2001-045470 | 2/2001 | | |
| JP | 2002-234574 | 8/2002 | | |
| JP | 2006-232294 | 9/2006 | | |
| JP | 2007-007128 | 1/2007 | | |
| WO | WO 2004080369 A1 * | 9/2004 | | A61J 1/00 |
| WO | 2007/144427 A2 | 12/2007 | | |

OTHER PUBLICATIONS

European Search Report mailed Oct. 5, 2011.
Japanese Office Action for Japanese Application No. 2013-515842, mailed Mar. 24, 2015.

* cited by examiner

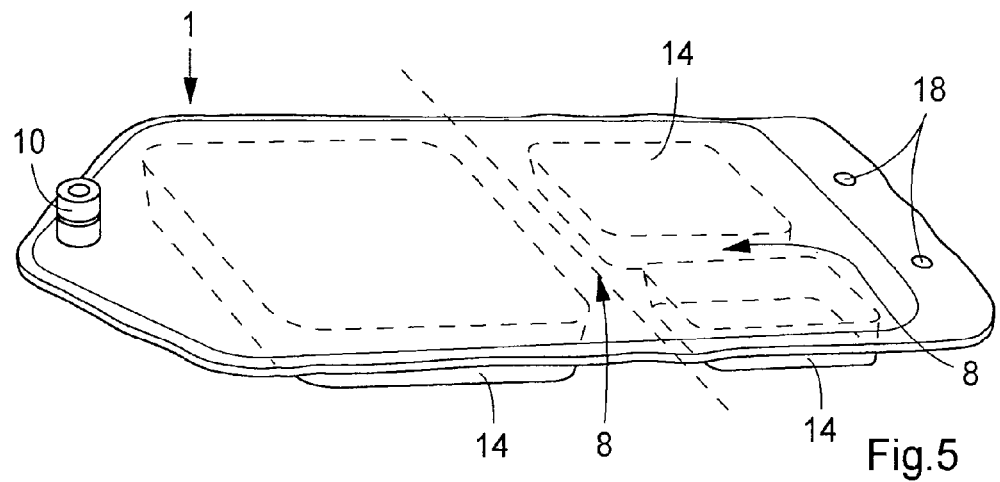
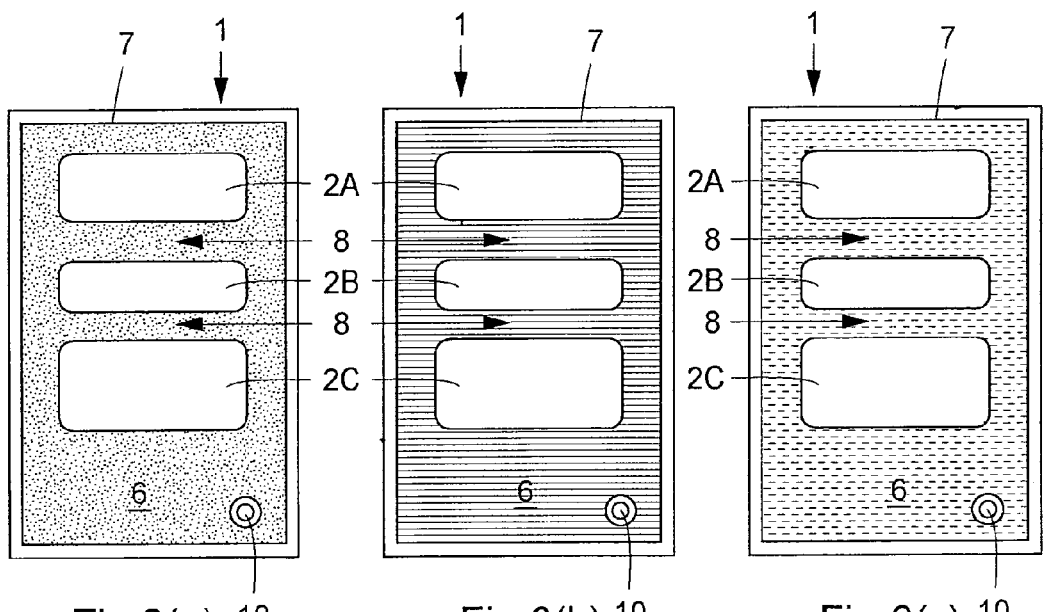
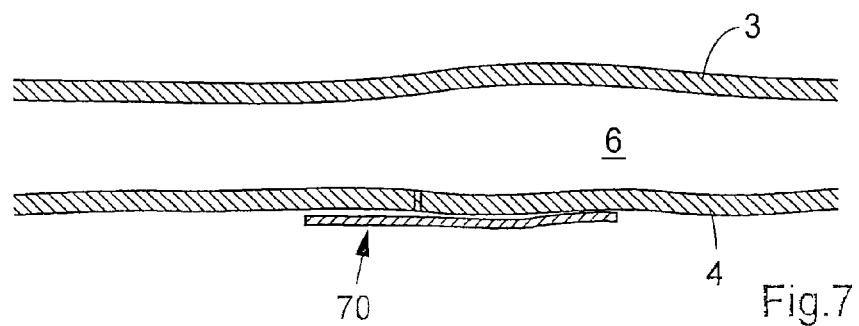

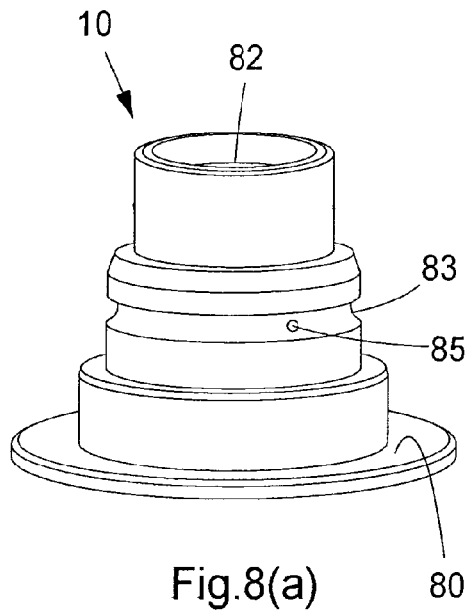
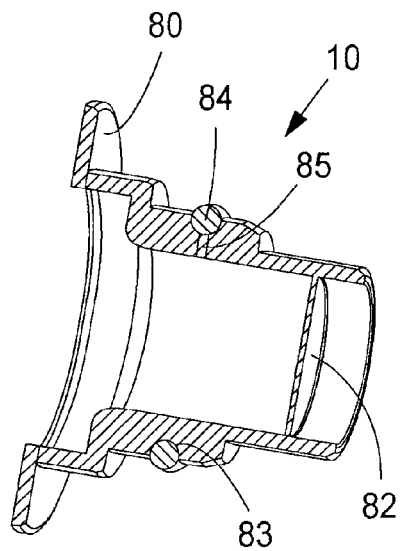
Fig.8(a)  Fig.8(b)
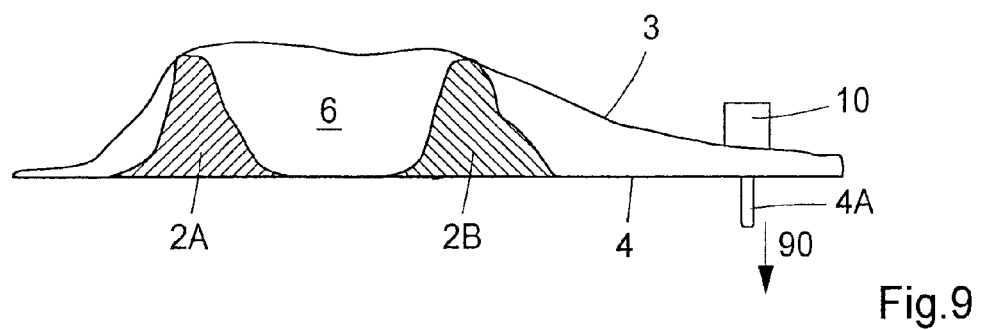
Fig.9

PREPARATION OF MEDICAL SOLUTIONS FROM POWDERY MATERIAL

TECHNICAL FIELD

The present invention relates to techniques for preparing medical solutions from powdery material, and in particular to packages for storing such powdery material.

BACKGROUND

One type of treatment for patients having substantially impaired renal function, or kidney failure, is known as "dialysis". Either blood dialysis ("hemodialysis") or peritoneal dialysis (PD) methods may be employed. Both methods essentially involve the removal of toxins from body fluids and restoration of such body fluids by diffusion and/or convection by means of a dialysis solution.

Patients receiving hemodialysis typically utilize 75 to 200 liters of prepared dialysis solution three times a week. The largest ingredient in these solutions is water.

Conventionally, dialysis solutions for hemodialysis are prepared from separate concentrated solutions. For example, one concentrate, Preparation A, includes a mixture of varied salts, sugars and acids dissolved in water. Another concentrate, Preparation B, is made of sodium bicarbonate dissolved in water, and may also contain sodium chloride. The constituents must be kept separate until shortly before hemodialysis because of the tendency for insoluble precipitates to form in the combined solution.

Even in concentrated solutions, the Preparations A and B are themselves bulky and difficult to transport. Moreover, bicarbonate solutions such as Preparation B have a tendency to form carbon dioxide and alter the pH of their solution over extended periods of time, even if not mixed with other components. Another logistical problem with preparing dialysis solutions is the need to keep the solutions essentially free of bacteria and endotoxins.

In peritoneal dialysis (PD), the patient's peritoneal cavity is filled with a dialysis solution. The dialysis solution is generally formulated with a high concentration of the dextrose, as compared to body fluids, resulting in an osmotic gradient within the peritoneal cavity. The effect of this gradient is to cause body fluids, including impurities, to pass through the peritoneal membrane and mix with the dialysis solution. By draining the spent dialysis solution from the cavity, the impurities are removed.

In PD, the dialysis solution is administered directly into the patient's body, and it is thus important that the dialysis solution is sterile and maintains the correct proportions and concentrations of components. Conventionally, for PD, dialysis solutions are delivered to the site of administration in pre-mixed solutions.

Similar to dialysis solutions for hemodialysis, the dialysis solutions used in PD are not stable over time due to incompatibility of the components in these solutions. For example, dextrose has a tendency to caramelize in solution over time, and bicarbonate ions react undesirably with calcium and magnesium in solutions to form insoluble calcium carbonate or magnesium carbonate. Bicarbonate can also spontaneously decompose into carbon dioxide and water.

Significant research efforts have been spent on providing dry formulations of components that are subsequently mixed with a solvent, typically water, to form dialysis concentrates or dialysis solutions. The use of dry formulations in the form of powdery material has the potential of increasing shelf life, reduce the formation of possible degradation products, and reduce the weight and volume of the material that needs to be transported to and stored at the dialysis treatment sites.

However, there are difficulties in using dry formulations for preparation of dialysis concentrates and dialysis solutions. For example, the preparation requires careful metering of the different formulations and solvent. It may also be necessary to take measures to ensure proper mixing and dissolution of the dry formulations in the solvent.

U.S. Pat. No. 4,664,891 discloses a system for preparation of a dialysis concentrate from dry chemicals and water. A disposable drum is selectively filled with dry chemicals in different layers, specifically such that an inner core of the drum is loaded with chemicals which form a slurry and/or dissolve slowly. In operation, a spray head is fitted over the drum and water is injected into the drum onto the chemicals within the inner core by the use of a nozzle, whereby the chemicals within the inner core are preferentially dissolved or form a slurry before other chemicals in the drum. Fluid is cycled through the drum until all of the chemicals in the drum have been dissolved and removed.

Another difficulty associated with the use of dry formulations is that certain components of the dry formulations are incompatible and therefore have to be stored separately. Some of the components, e.g. magnesium chloride, calcium chloride and glucose, typically bind water molecules, at least in their commonly used forms, while other components, e.g. NaCl, are hygroscopic. If the former component(s) releases water during storage, the latter component(s) may form lumps or cakes, and these lumps/cakes may be difficult to dissolve when preparing the dialysis solution. If bicarbonates and acids are mixed, gases may be formed in the presence of water. If glucose and acids are mixed and subject to non-dry conditions, the glucose may be degraded and discolored.

Another way to ameliorate the problem is to store the different components in separate packages. However, this leads to an elevated risk for incorrect composition of the dialysis solution due to incorrect handling. Typically, a complicated apparatus needs to be used to ensure proper preparation.

Yet another solution is proposed in US2006/0115395, which discloses an apparatus for producing a peritoneal dialysis solution from dry reagents. The dry reagents are separated into compatible groupings, denoted reagent beds, which are placed in separate compartments within a disposable housing. The disposable housing defines a fluid flow path through the sequence of separate compartments. Each compartment is arranged between an upstream and a downstream compression component, and the reagent beds are constrained from movement within the housing by reagent bed restraints, which have a fine enough porosity to prevent the passage of reagent particles in their dry form while allowing a liquid diluent to pass. In operation, the diluent is fed to the housing to flow along the fluid flow path and dissolve the reagents. The compression components apply continuous compressive force on either side of the reagent bed to pack the reagents close together as the reagent particles are dissolved.

The housing in US2006/0115395 is a disposable of complex design involving a combination of several different materials at significant amounts. The disposable is not only costly and fairly complicated to manufacture, but it may also require non-standard processing for waste handling/recycling. Further, it is not unlikely that the apparatus in US2006/0115395 may produce a dialysis solution of varying composition, since its operation relies on a continuous dissolution of the dry reagents while the diluent flows through the housing. Any lack of dissolution or any accumulation of poorly dissolved reagents in the compression components or on restraints may be difficult to identify by visual inspection.

The prior art also comprises WO2007/144427, which discloses a container that includes a plurality of compartments separated by compartment dividers which rupture when a sufficient pressure is applied by a liquid or gas introduced into the container. Some of the compartments comprises powder which dissolves at the introduction of liquid into the container. The container is a disposable of complex design. Further, the dividers must be designed to open/rupture in a controlled and reproducible way to avoid incomplete dissolution of the powder.

Although the foregoing discussion is given in relation to preparation of dialysis solutions, it is to be understood that corresponding problems and needs are equally and generally valid for the preparation of other types of medical solutions, such as replacement solutions, infusion solutions or nutritional solutions.

SUMMARY

It is an object of the invention to at least partly overcome one or more of the limitations of the prior art.

In view of the foregoing, one object is to enable preparation of a medical solution from powdery material. It is another object to enable a technique for preparation which is simple to practice. A further object is to enable a technique for preparation which is likely to give consistent quality of the medical solution. Yet another object is to enable a significant shelf life of the powdery material.

A still further object is to provide a package for powdery material to be used in preparation of a medical solution, where the package is easy to manufacture. Another object is to provide such a package for powdery material which has a low manufacturing and material cost. Yet another object is to provide such a package for powdery material which is easy to recycle.

One or more of these objects, and further objects that may appear from the description below, are at least partly achieved by means of a package for storing powdery material, a method of manufacturing the package, a method of preparing a medical solution, and uses of the package according to the independent claims, embodiments thereof being defined by the dependent claims.

A first aspect of the invention is a package for storing powdery material which is to be mixed with a solvent to form a medical solution. The package comprises: a compartment which is at least partially defined by two opposing wall portions and contains the powdery material in the form of at least two distinct sets of powdery material of different compositions, wherein the opposing wall portions are brought into engagement with the powdery material so as to immobilize the sets of powdery material; and a connector for selectively admitting a fluid into the package for expanding the compartment and enabling mixing of the sets of powdery material with the solvent in the compartment as part of a process for preparing the medical solution.

Thus, according to the first aspect the powdery material is stored in a single compartment within the package, in two or more distinct sets of different compositions. Each set is distinct in the sense that it is distinguishable from the other set, by its location and/or by its composition. As used herein, "different compositions" denotes compositions that differ in what substances that make up the powdery material and/or by the relative amounts of the substances that make up the powdery material and/or by the distribution of particle sizes in the powdery material. By bringing the opposing wall portions of the compartment into engagement with the powdery material, the distinct sets are immobilized within one and the same compartment. This means that any significant mixing or migration of powdery material between the sets is prevented or at least impeded. Thus, it is realized that the package according to the first aspect allows storage of incompatible components within one and the same package, without the need to provide specific restraints to partition the package into separate compartments. It is likewise realized that the package according to the first aspect also may be used for storage of components that are compatible with each other, e.g. to profit from any other advantage of the package, e.g. as explained below.

Furthermore, the compartment is expandable by admission of e.g. a fluid so that the preparation of the medical solution may take place inside the compartment. The expansion of the compartment releases the immobilization of the distinct sets of powdery material, whereby the sets of powdery material may be mixed with each other and with a solvent inside the expanded compartment to form the medical solution. Thus, it can be seen that the package of the first aspect provides a temporary immobilization of distinct sets of powdery material, e.g. during transportation and storage, while still allowing mixing of the distinct sets of powdery material with a solvent inside the package at the time of preparation.

The expansion may be caused by admission of a gas, e.g. air, or by admission of the actual solvent that is used for preparing the medical solution. It is also conceivable that the solvent is mixed with a gas when admitted into the compartment e.g. to improve the mixing with the powdery material inside the compartment.

The package can be manufactured with a minimum of material, since the distinct sets may (but need not) be immobilized solely by their engagement with wall portions of the compartment. Furthermore, the package may be made from a single material or only a few different materials, which facilitates both manufacture and subsequent recycling.

The package may contain the powdery material in carefully metered doses. By controlling the amount and quality of the solvent admitted into the compartment, the concentration and composition of prepared medical solution will be well-defined. An improved consistency of the medical solution is achieved by the fact that there are no dividers that need to be ruptured or otherwise opened before mixing is allowed to take place, but instead at least part of the dissolution and mixing of the powdery material may take place inside a single compartment.

In contrast to prior art techniques that rely on dissolution and mixing into a flowing solvent, the inventive package allows the solvent to enter and stay in the compartment until the powdery material is fully dissolved and the mixing is complete. This may simplify the preparation of the medical solution and obviate the need for specific measures to improve mixing and dissolution, such as the use of dedicated spray nozzles, mechanical stirring devices or recirculation systems (although such measures may be implemented in certain embodiments). In the inventive package, the dissolution and mixing may be aided by simply kneading, squeezing or shaking the package.

However, it is to be understood that the dissolution and mixing may be supported in other ways. For example, the package may be connected to a circulation system which is operated to repeatedly extract and re-introduce at least part of the solvent from and to the compartment, respectively. It is also conceivable that the preparation of the medical solution is finalized outside the compartment, e.g. by further mixing or by adding further substances to the solution produced by the dissolution and mixing process. Still further, the mixing and dissolution process may be supported by measurements to determine when a proper solution has been obtained, e.g. by means of conductivity measurements, as is well-known in the art.

In one embodiment, the package is wholly or partially manufactured of transparent material, to enable visual inspection to verify that the dissolution and mixing is complete.

The package may contain any combination of powdery material, and it may thus be used for preparation of any conceivable medical solution. Non-limiting examples of medical solutions include dialysis concentrates, dialysis solutions, infusion solutions, nutrition solutions, replacement solutions, and plasma expander solutions. The inventive package also makes it possible to produce a fluid with substances that are unstable during long term storage in fluids such as, but not limited to, NAG (N-Acetylglucosamine), antioxidants like vitamin C, and amino acid containing molecules like peptides and proteins.

The engagement between the opposing wall portions and the sets of powdery material in the package may be achieved in different ways during manufacture of the package.

In one embodiment, at least one of the opposing wall portions is deformed into the engagement with the powdery material. The thus deformed wall portion(s) may be made of a material that inherently retains its deformed shape. Such materials include metallic foils or laminates, e.g. of aluminum, or thermoplastics which are deformed by cold forming or heat forming. Such an embodiment requires the admitted fluid to push the deformed wall portion(s) out of engagement with the powdery material. Alternatively or additionally, one or both wall portions may be made of flexible material, which easily can be brought into and out of the engagement. When one or both wall portions are made of flexible material, the package is generally supplemented by a means for maintaining the engagement, since the material has little ability to retain the engagement by itself. Non-limiting examples of materials for the opposing wall portions include polyolefin materials such as polypropylene (PP), polyethylene (PE), polyamide (PA), cyclic olefin copolymer (COC), polystyrene (PS), styrene-ethylene-butylene-styrene triblock copolymers (SEBS), styrene-ethylene-propylene-styrene triblock copolymers (SEPS), laminated or homogeneous, with a thickness of about 0.1-0.5 mm, preferably about 0.25-0.3 mm. The material may further have a water vapour transmission rate less than 0.3 g/m$^2$/day at 38° C./90% RH, or even less than 0.2 g/m$^2$/d at 38° C./90% RH.

Irrespective of wall portion material and properties, a pressure difference may be applied between the interior and the exterior of the compartment to bring the wall portions into the engagement. In one embodiment, the wall portions are thus brought into the engagement by actively evacuating a gas, e.g. air, from the compartment, at least in the space surrounding the powdery material. In another embodiment, the sets of powdery material are arranged between the wall portions in a low pressure environment, e.g. in a vacuum chamber, whereby the wall portions are pressed into the engagement by the atmospheric pressure when the package is moved from the low pressure environment into an ambient atmosphere.

Irrespective of wall portion material and properties, the package may be evacuated such that the compartment holds a sub-atmospheric pressure. It is currently believed that the provision of a sub-atmospheric pressure in the compartment will further limit any migration of moisture from one set to another inside the compartment. Furthermore, the sub-atmospheric pressure serves to make the package tamper proof. Any opening, puncture or rupture of the package during transport or storage can be detected by a lack of sub-atmospheric pressure in the compartment. Furthermore, if one or both of the wall portions are of flexible material, the sub-atmospheric pressure will serve as a means for retaining the engagement between the wall portion(s) and the powdery material. According to one non-limiting example, the compartment may be evacuated to at least a pressure of about 50-200 mmHg (about 6.5-26.5 kPa) below atmospheric pressure.

In one embodiment, the compartment is evacuated such that the powdery material is at least partially compacted, so as to reduce the spacing between the particles of the powdery material. This will serve to further immobilize the powdery material in the compartment.

In one embodiment, the sets of powdery material are stacked on each other in the compartment. Thus, each set is not only immobilized by engagement with the opposing wall portions, but also by being brought into contact with at least one other set. If the powdery material is separated into at least three sets it may be preferable to arrange the sets so as to optimize the compatibility between adjacent sets, i.e. to space the sets that are the most incompatible. In the context of the present disclosure, incompatible materials are defined as materials that cause at least one of the materials to deteriorate or to change physical state (e.g. by lumping or caking) when they are mixed or brought into close contact.

In another embodiment, the sets of powdery material are spaced from each other in the compartment. The spacing serves to isolate the sets from each other, thereby reducing the interaction between the different sets. This will serve to increase the freedom of placement of the different sets in the compartment, although it may still be advantageous to optimize the locations of the sets based on their mutual compatibility.

It is also possible to combine stacking and spacing of the sets in the compartment, if the powdery material is separated into more than two sets.

In an embodiment with spaced sets of powdery material, the compartment is at least partly defined between two opposing sheets, and at least two of the spaced sets are separated by a constriction region, in which the sheets are brought into close proximity with each other without being fixedly attached to each other. The sheets typically define both the wall portions that engage each set to immobilize the powdery material, as well as a region that forms an "open barrier" between the sets. The open barrier is formed as a constriction that serves to prevent or at least impede migration of powdery material between the spaced sets. The use of a constriction region allows the spaced sets to be confined and immobilized within a single compartment while essentially preventing mixing between the different sets.

In one embodiment, the opposing sheets are brought into contact with each other in the constriction region, so as to effectively block migration of powdery material. However, it is conceivable that there is a spacing between the sheets in the constriction region, provided that the spacing is sufficient to significantly impede migration of powdery material.

In one embodiment, the maximum distance between the opposing sheets in the constriction region is less than an effective minimum diameter of the powdery material. Powdery materials generally has a distribution of particle sizes, and the "effective minimum diameter" is to be understood as a size value in the lower end of the particle size distribution for sets that are separated by the constriction region. Thus, the effective minimum diameter may be given by the 20th percentile, or less, of the particle sizes within a set. As used herein, a percentile indicates the corresponding percentage of the total mass of particles that has the smallest particle sizes, and thus the effective minimum diameter is given by the maximum particle size in such a percentage. Typically, the effective minimum diameter is given by the 15th percentile, the 10th percentile, the 5th percentile, the 4th percentile, the 3rd percentile, the 2nd percentile or the 1st percentile, or an even smaller percentile.

It is also to be understood that the maximum distance may be selected in dependence of the incompatibility of the sets that are separated by the constriction region, where a lesser degree of incompatibility may allow for the maximum distance to match a higher percentile, whereas a higher degree of incompatibility may require the maximum distance to match a lower percentile.

It is to be understood that the particle size distribution for a powdery material may vary from batch to batch. However, the distribution is generally selected to achieve one or more properties that are relevant for the subsequent preparation of the medical solution, such as solubility rate and wettability, as well as one or more properties that are relevant for the manufacture, transport and storage, such as flow properties, packing characteristics, caking tendency, compression characteristics, and appearance. In examples relevant for powdery materials used in preparation of dialysis solutions/concentrates, the effective minimum diameter may be about 500 µm, 250 µm, 200 µm, 150 µm, 100 µm, 75 µm or 50 µm.

In one embodiment, the package is folded so as to form a fold or bending in the constriction region. The fold will serve to further impede migration of powdery material or other components thereof, such as water, between the sets.

In one embodiment, the package further comprises means for reducing adhesion between the sheets in the constriction region. Such means will improve the ability of the compartment to be expanded in the process of preparing the medical solution, and thus to ensure proper mixing of the sets of powdery material with the solution.

In one embodiment, the means for reducing adhesion comprises a three-dimensional surface pattern facing the constriction region on at least one of the sheets. Such a three-dimensional surface pattern will decrease the affinity of the sheets to stick together, and will facilitate both expansion of the compartment and proper evacuation of the compartment, if used for providing the aforesaid engagement. Preferably, the depth of the surface pattern is selected such that the maximum distance between the sheets in the constriction region is less than the effective minimum diameter of the powdery material. In view of the typical particle sizes of powdery material used in preparation of e.g. dialysis solutions, the surface pattern may have a depth of less than about 50 µm, 40 µm, 30 µm, 20 µm, or 10 µm.

In order to further limit any migration of powdery material between the spaced sets, and to potentially be able to use a rather large depth of the surface pattern, the surface pattern may be defined so as to not form any channels or paths that extend between the spaced sets, or at least not any straight channels/paths. In one embodiment, the surface pattern is defined by elongate ridges that extend essentially perpendicularly to a direction of separation between the spaced sets.

In one embodiment, the means for reducing adhesion comprises a respective composition of the sheets for low mutual adhesion. It is to be understood that this embodiment may be combined with the above-mentioned surface structure.

In one embodiment, at least one of the sets of powdery material is arranged in a predefined pocket inside the compartment. It is to be noted that the pocket does not fully enclose the set, since all the sets are arranged in a single compartment, but rather limits the movement of the set of powdery material. The limited movement may facilitate the loading of the sets into the compartment during manufacture of the package, and/or serve to further limit movement of the set when engaged in the compartment by the opposing wall portions.

In one embodiment, the pocket is at least partially defined by an internal partition extending into the compartment from a closed perimeter portion of the compartment. Thereby, the pocket can be formed by the addition of a minor partition, since a significant portion of the pocket will be defined by the existing perimeter portion. Furthermore, two pockets may be defined by a single intermediate partition, and these pockets will open towards a common volume in the compartment. The common volume may serve as a mixing zone, in which the powdery materials may mix with each other and with the solvent after the expansion of the compartment. Irrespective of pocket design, it is conceivable to arrange a plurality of pockets with their opening facing such a mixing zone in the compartment.

When the compartment is at least partly defined between two opposing sheets, the or each internal partition may be formed by fixedly attaching the sheets to each other, e.g. by means of a weld line, glue or any alternative or equivalent permanent fixation means.

Alternatively or additionally, the pocket may be at least partially defined by an internal corner portion at the perimeter of the compartment. Such a pocket design makes use of existing shapes in the compartment to limit the movement of the powdery material when engaged between the opposing wall portions.

In another embodiment, the pocket is formed as a tray-shaped deformation in one of the opposing wall portions that engage the powdery material.

In one embodiment, the package further comprises a check valve in fluid communication with the compartment to enable evacuation of the compartment. Such a check valve is thus mounted to be automatically closed by the pressure difference that is applied over the check valve when the compartment is evacuated to a sub-atmospheric pressure. In another embodiment, the compartment is evacuated via a hollow needle inserted into the compartment through one of its walls, where the resulting hole in the wall is sealed by any appropriate means (tape, heat sealing, glue etc) after retraction of the needle.

In yet another embodiment, the compartment is evacuated via the connector. To facilitate such evacuation, a check valve may be integrated with the connector to enable the evacuation.

A second aspect of the invention is a method of manufacturing a package for storing powdery material which is to be mixed with a solvent to form a medical solution. The method comprises: arranging the powdery material in a compartment which is at least partially defined by two opposing wall portions, wherein the powdery material is arranged in the form of at least two distinct sets of powdery material of different compositions; providing a connector for selectively admitting a fluid into the package for expanding the compartment and enabling mixing of the sets of powdery material with the solvent in the compartment as part of a process for preparing the medical solution; and bringing the opposing wall portions into engagement with the powdery material so as to immobilize the sets of powdery material.

The second aspect shares the advantages and technical effects of the first aspect. It is also to be understood that the method of manufacturing may involve forming, installing or otherwise providing any of the features defined in the above-mentioned embodiments of the first aspect.

A third aspect of the invention is a method of preparing a medical solution. The method comprises: obtaining a package that comprises a compartment which is at least partially defined by two opposing wall portions and contains powdery material in the form of at least two distinct sets of powdery material of different compositions, wherein the opposing wall portions are brought into engagement with the powdery material so as to immobilize the sets of powdery material, and a connector for admitting a fluid into the package; connecting the connector to a source of a solvent; and selectively admitting the solvent into the package, whereby the compartment is expanded and the solvent mixes with the sets of powdery material inside the compartment as part of a process for preparing the medical solution.

The third aspect shares the advantages and technical effects of the first aspect. It is also to be understood that the method of preparing may involve using, obtaining, causing or otherwise providing any of the features defined in the abovementioned embodiments of the first aspect.

A fourth aspect of the invention is a use of the package according to the first aspect in peritoneal dialysis treatment.

A fifth aspect of the invention is a use of the package according to the first aspect in blood dialysis treatment.

Still other objectives, features, aspects and advantages of the present invention will appear from the following detailed description, from the attached claims as well as from the drawings.

BRIEF DESCRIPTION OF THE DRAWINGS

Embodiments of the invention will now be described herein by way of example only, with reference to the accompanying schematic drawings.

FIG. 5 is a perspective view of another exemplifying package.

FIG. 6(a)-(c) are plan views to illustrate different types of surface structures.

FIG. 7 is a section view of a check valve for a package.

FIG. 8(a)-(b) are perspective and section views, respectively, of another check valve for a package.

FIG. 9 is a side view to illustrate the use of a pull tab on a package.

DETAILED DESCRIPTION OF EXEMPLARY EMBODIMENTS

Figure 1A:
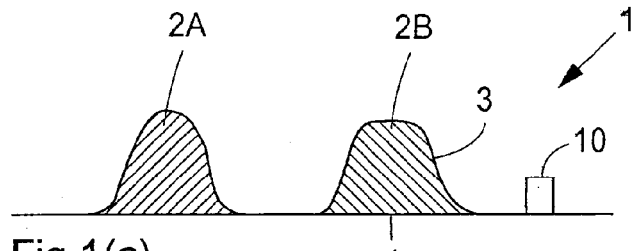
FIGS. 1(a)-(b) are side and plan views of an exemplifying package.

Exemplary embodiments of the present invention will now be described with reference to packages that are produced by evacuation and used for preparation of dialysis solutions. However, it is to be appreciated that the technology to be described is not limited to such implementations and uses, but may apply alternative production methods and be used for preparation of any type of medical solution.

Throughout the description, the same reference numerals are used to identify corresponding elements.

Figure 1B:
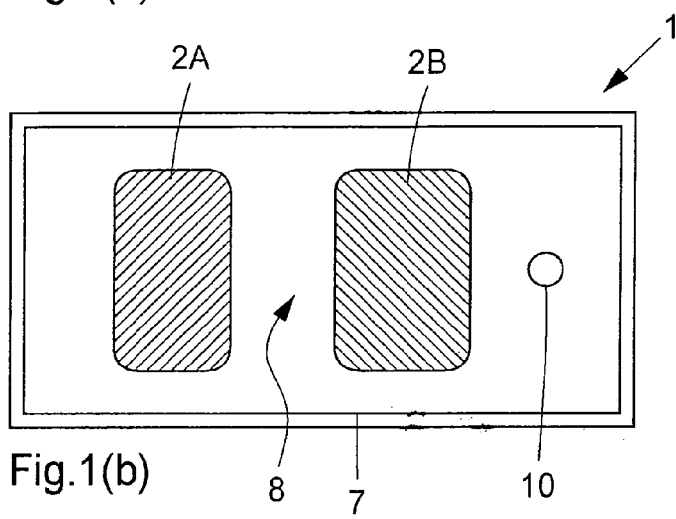

FIGS. 1(a)-(b) are a side view and a plan view, respectively, of a package or bag 1 that contains powdery material for use in preparation of a dialysis solution or concentrate to be further diluted to a ready for use dialysis solution, hereinafter collectively referred to as dialysis solution. The combined storage and preparation package 1 is shown in a transport/storage state, i.e. before preparation of the dialysis solution. The powdery material is separated into two powder groups 2A, 2B of different compositions. The powder groups 2A, 2B are spaced from each other, and each powder group 2A, 2B contains either a single dry substance or a combination of compatible dry substances. In this context a "dry substance" denotes a substance in solid form. It should be noted that a dry substance may still contain water, e.g. if the water molecules are incorporated in a crystal lattice, so-called water of crystallization.

The powder groups 2A, 2B are arranged between two sheets or foils 3, 4 that define a single compartment 6, as shown in FIG. 1(b). In the example of FIG. 1(b), the sheets 3, 4 are merged to define the compartment 6 by means of a circumferential weld line 7. The compartment 6 is collapsed such that opposing sheet portions are brought to engage the respective powder group 2A, 2B. The resulting pressing forces serve to immobilize the powder groups 2A, 2B. Between the powder groups 2A, 2B there is a constriction region or zone 8, which is formed by opposing sheet portions being brought into close proximity or abutment with each other, such that migration of powder between the powder groups 2A, 2B is prevented or at least significantly obstructed. The package 1 further includes a connector 10 which is in fluid communication with the compartment 6. The connector 10, which is sealed in the transport/storage state, is adapted for connection to a supply of a solvent, typically water. Thus, in a preparation state of the package 1, the engagement between the sheets 3, 4 and the powder groups 2A, 2B is released, either before or as a result of the solvent entering the compartment 6 via the connector 10. The solvent flows into the compartment 6 and the powdery material is mixed with and dissolved in the solvent to form the dialysis solution.

Figure 1C:
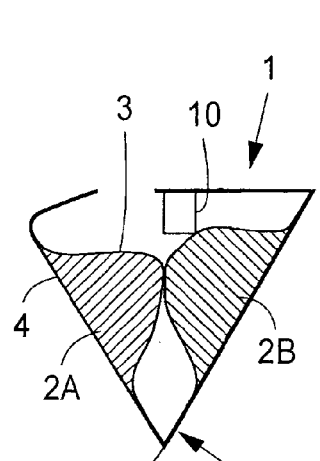
FIG. 1(c) is a side view of the package in FIG. 1(a)-(b) after folding.

In a variant, the package 1 is folded in the transport/storage state, e.g. to facilitate the handling of the package. As shown in the side view of FIG. 1(c), it may be advantageous to provide a fold 12 in the constriction region 8, since the fold 12 will serve to further obstruct any migration of powder between the groups 2A, 2B. Further, folding the powder groups 2A, 2B and the connector 10 towards each other may serve to protect these protruding parts of the package and to provide a smoother outer contour of the package, thereby reducing the risk for damage during transport/storage. Furthermore, the package 1 may be designed and folded such that the most hygroscopic powder group or the powder group with the highest water content is located at the center of the folded package, i.e. is wrapped by the largest number of sheets to impede undesired propagation of moisture within the package.

Figure 1D:
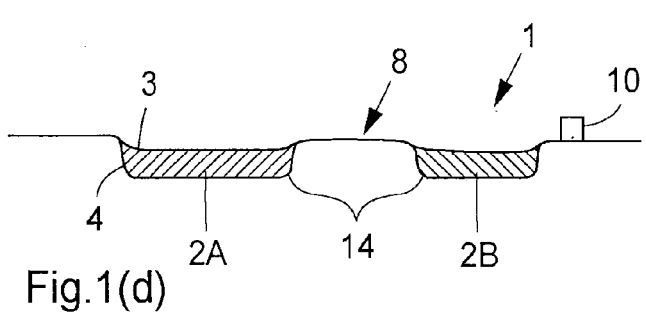
FIG. 1(d) is a side view of another exemplifying package.

FIG. 1(d) illustrates a package 1 in which powder groups 2A, 2B are located in preformed trays 14 in the bottom sheet 4. Such a configuration may facilitate the manufacture of the package, since the trays 14 will define the location of each powder group 2A, 2B and may serve to keep the powder groups 2A, 2B in place during manufacture of the package, especially during an evacuation of the compartment 6. The provision of trays 14 may also serve to obstruct migration of powder in the transport/storage state.

Figure 1E:
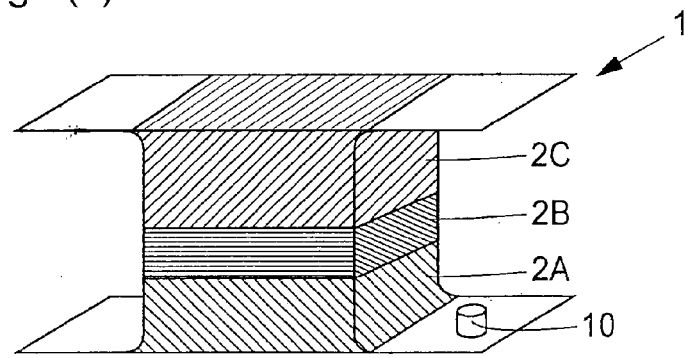
FIG. 1(e) is a perspective view of another exemplifying package.

FIG. 1(e) illustrates a package 1 in a transport/storage state, in which powder groups 2A-2C are stacked on each other. The compartment is evacuated to tightly squeeze the powder groups 2A-2C between opposing sheet portions, whereby the powder groups 2A-2C are immobilized within the single compartment. By immobilizing the powder groups 2A-2C in relation to each other, and thereby minimizing mixing between the powder groups 2A-2C, it might even be possible to arrange incompatible powder groups in contact with each other. If the package contains three or more powder groups, it may however be preferable to arrange the powder groups so as to optimize the compatibility between neighboring powder groups. In the example of FIG. 1(e), a highly hygroscopic powder group 2A may be spaced from a water containing powder group 2C by a less (or non-) hygroscopic powder group 2B with a lower (or no) water content. The intermediate powder group 2B will thus serve as a moisture barrier.

As indicated in the foregoing, many embodiments of the invention involve an evacuation of the compartment 6 with respect to gases (e.g. air) present in the surroundings of the powder groups. The evacuation may also involve removal of gases within the powder groups, e.g. for compacting the powdery material. It is to be noted that depending on implementation the evacuation may or may not reduce the pressure inside the compartment 6 below atmospheric pressure.

If at least one of the sheets 3, 4 is flexible, it may be advantageous to establish a sub-atmospheric pressure inside the compartment 6 during the evacuation and to retain this pressure in the transport/storage state so as to retain the engagement between the sheets and the powdery material. Alternatively, external means may be used to retain the engagement. For example, a shrinkwrap or overwrap (not shown) may be applied onto the exterior of the package to press the sheets against the powdery material.

If the sheets 3, 4 are made of essentially non-flexible material, the evacuation may establish a required pressure to deform the sheets into engagement with the powder groups. After the deformation, the sub-atmospheric pressure may be released, if the sheets 3, 4 are sufficiently stable to retain the engagement with the powder groups in the absence of sub-atmospheric pressure.

It can be noted that a sub-atmospheric pressure may be retained in the compartment 6 in the transport/storage state for other reasons, e.g. to reduce migration of moisture between the powder groups and/or to tamper proof the package 1.

The evacuation may be achieved by actively sucking gases out of the compartment 6 during manufacture, or by applying external forces to press the sheets 3, 4 towards the powder groups and thereby pressing gases out of the compartment 6. Alternatively, the compartment 6 may be manufactured in a sub-atmospheric environment, e.g. in a vacuum chamber. Different techniques for manufacturing the package will be exemplified further below with reference to FIGS. 10-13.

Figure 2A:
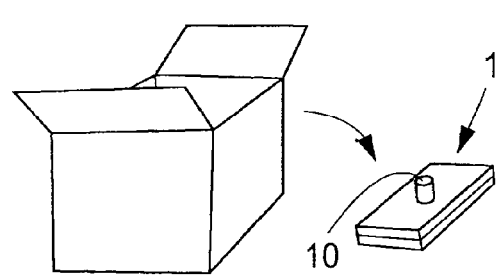
FIG. 2(a)-(e) illustrate a sequence of steps when using a package for preparing a medical solution.
Figure 2B:
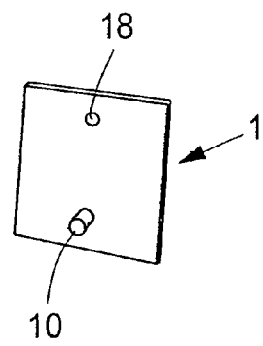
Figure 2C:
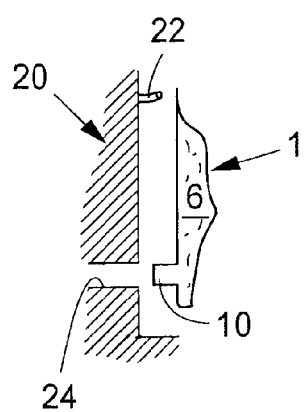
Figure 2D:
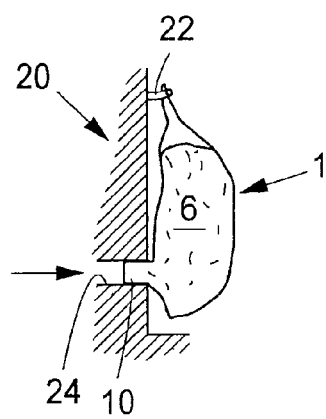
Figure 2E:
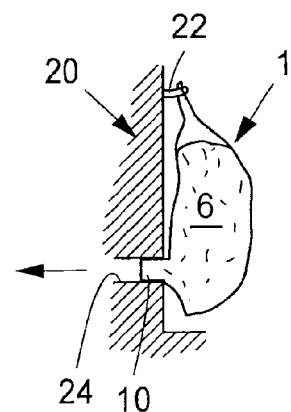

FIG. 2(a)-(e) exemplifies the use of an example package 1 for preparation of a dialysis solution. The package 1 is delivered at the dialysis site in the transport/storage state, FIG. 2(a). In the illustrated example, the package 1 is both evacuated and folded. The package 1 is transformed into a preparation state by unfolding the package 1 and opening the connector 10 to admit air (or a fluid/solvent) into the compartment 6, FIG. 2(b). The package 1 is then mounted on a stand 20, which may or may not be part of a dialysis machine. In the example of FIG. 2(c), the package 1 is suspended by threading a suspension hole 18 formed in the periphery of package 1 over a hook 22, such that the powdery material falls down at the bottom of the compartment 6, and the connector 10 is mated within an opening 24 connected to a water supply (not shown). In FIG. 2(d), the water supply is operated to push a carefully metered volume of water into the compartment 6, whereby the compartment 6 is expanded and the powdery material is dissolved in the water to form the dialysis solution. Finally, in FIG. 2(e), the dialysis solution is extracted from the package 1.

Below, further variants of the package 1 and its structural features will be described with reference to FIGS. 3-8.

Figure 3:
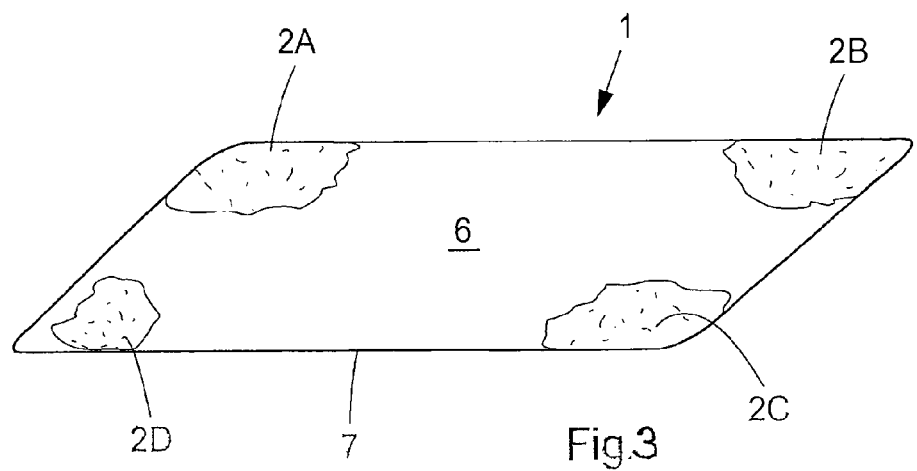
FIG. 3 is a perspective view of another exemplifying package.

FIG. 3 illustrates a rectangular package 1 in which powder groups 2A-2D are arranged at the corners of the compartment 6. Thereby, the corner portions may assist the pressing forces exerted by the sheets 4 to restrain any movement of the powdery material. It is to be realized that the package 1 can be designed with any given number of corners to accommodate a corresponding number of powder groups 2A-2D. For example, the package 1 may have the shape of a triangle or a star.

Figure 4A:
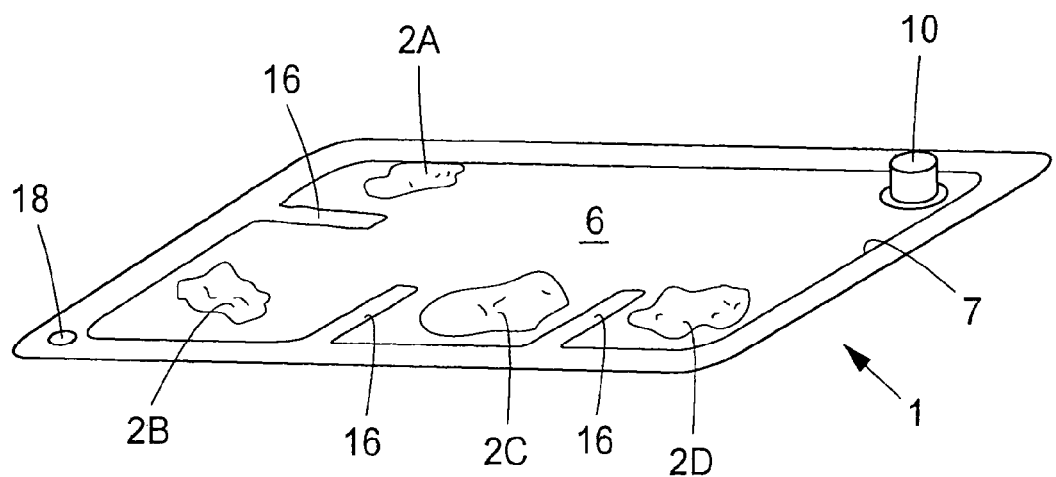
FIG. 4(a)-(b) are perspective views of another exemplifying package in a transport/storage state and a preparation state, respectively.

FIG. 4(a) illustrates a package 1 which is provided with internal partitions 16 that extend from the peripheral weld line 7. The partitions 16 define pockets for holding powder groups 2A-2D in the transport/storage state, as illustrated. The pockets may be used to facilitate separation of the powder groups 2A-2D when the package 1 is filled and evacuated during manufacture. The pockets may also assist the pressing forces exerted by the sheets to prevent mixing between the powder groups 2A-2D.

Figure 4B:
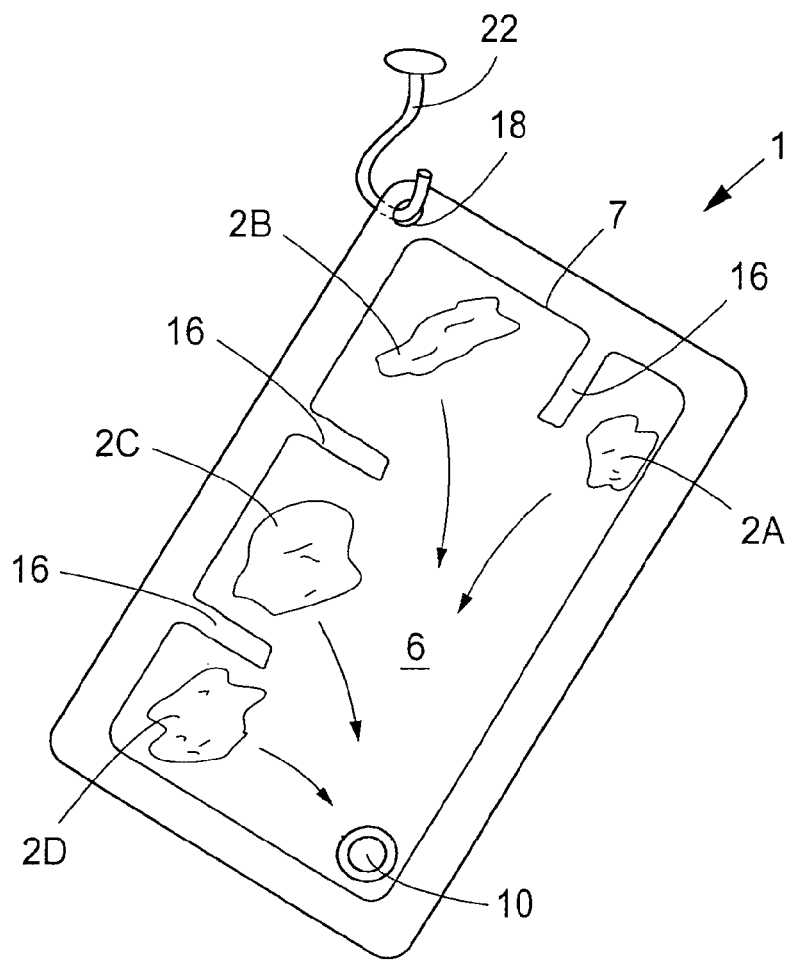

FIG. 4(b) illustrates the package of FIG. 4(a) in a preparation state, in which the connector 10 has been opened to admit air or a fluid/solvent into the compartment 6 to release the pressing forces on the powder groups 2A-2D. In the preparation state, the package is suspended from a suspension hole 18 arranged at one end of the package 1 behind the pockets, i.e. outside the peripheral weld line 7, such that the pockets are emptied by the action of gravity. The powder groups fall down into a common mixing zone within the compartment 6. It may be preferable to convey the powder groups 2A-2D into the mixing zone before admitting the solvent into the compartment 6, to ensure that all of the powdery material is properly mixed with and dissolved in the solvent and to avoid that some powdery material gets stuck at any corner portion in the compartment 6. For the same reason, it may also be preferable to arrange the connector 10 and the suspension hole 18 at opposite ends of the package 1, such that the solvent is admitted directly into the mixing zone when the package 1 is in the suspended preparation state.

FIG. 5 is a perspective view of a variant of the package in FIG. 1(d), where the powdery material is placed in a respective tray 14 which is formed as a permanent depression in the bottom sheet. Like the embodiment in FIG. 4(b), suspension holes 18 and the connector 10 are arranged at opposite ends of the package 1 to ensure that the solvent is admitted into the mixing zone formed at the bottom of the suspended package 1. It can also be noted that the largest tray 14 is arranged at the mixing zone to minimize the provision of corner portions in the mixing zone.

In the preparation state, it is generally desirable for the compartment 6 to quickly and easily expand in order to ensure a good mixing of the powder groups. FIGS. 6(a)-(c) illustrate the use of a structured sheet surface to facilitate separation of the sheets in the constriction regions. The surface structure may be applied to one or both of the sheet portions that form the constriction regions 8, e.g. in the form of an embossed pattern. The surface height of the surface structure may be selected so that the spacing between the sheet portions significantly impedes migration of powdery material across the constriction regions 8. In FIG. 6(*a*), the pattern is formed as protruding dimples, giving the surface a dotted appearance. In FIG. 6(*b*), the pattern is formed as elongate ridges. The ridges are arranged not to form channels between the powder groups. This will allow the height of the ridges to be selected independently of the particle size in the powder groups 2A-2C. FIG. 6(*c*) illustrates yet another example of a surface structure in which short ridges are arranged in mutually offset rows to provide a meandering pattern of channels across the constriction regions 8 between the powder groups 2A-2C. Such a meandering pattern will serve to obstruct migration of powdery material across the constriction regions 8.

In FIG. 6, the surface pattern is provided not only in the construction regions 8 but across the entire sheet. This may be preferable for reasons of manufacture, to avoid the need to match the pattern to the locations of the powder groups 2A-2C. Furthermore, the provision of a surface pattern across the major extent of the compartment 6 may serve to facilitate evacuation of the compartment 6 during manufacture, by reducing the tendency for the sheets to be sucked together locally within the compartment 6 by the forces of evacuation.

The evacuation of air from the compartment 6 may be done through a separate evacuation port in one of the sheets, which port is closed after the evacuation by e.g. welding or application of a tape. Alternatively, the evacuation port may be automatically closed after evacuation by the resulting pressure difference. Such an evacuation port may be implemented as a check valve.

FIG. 7 illustrates a check valve 70 which is integrated into one of the sheets (here, the bottom sheet 4) that define the compartment 6.

FIGS. 8(*a*)-(*b*) are perspective and section views, respectively, of a connector 10 with an integrated check valve function. In the illustrated embodiment, one end of the connector has a flange 80 which is arranged for mounting, e.g. by welding or gluing, in alignment with an opening in a wall portion of the compartment. In the other end of the connector 10, a membrane 82 is arranged to seal the opening of the connector 10. The membrane 82 is further arranged to be penetrated at connection of a standard connector (not shown) on a line set in fluid communication with e.g. a dialysis machine or a catheter for peritoneal dialysis. A recess 83 for an o-ring 84 is formed in the outer periphery of the connector 10. The o-ring 84 is covering (and sealing) a small hole 85 which is in fluid communication with the interior of the connector 10 and thus with the compartment. The combination of the o-ring 84 and the hole 85 has the function of a check valve. When a suction is applied on the outside of the connector 10, the o-ring 84 moves away from the hole 85 to allow air to be sucked out of the compartment, and when the negative pressure is removed the o-ring 84 closes the hole 85 and prevents air from re-entering the compartment.

FIG. 9 illustrates a technique to facilitate evacuation of the compartment via an evacuation port, be it the connector 10 (as shown) or a separate opening. FIG. 9 illustrates an embodiment of the package 1 before evacuation, where a pull tab 4A is attached to the sheet portion opposite to the evacuation port 10. The pull tab 4A may be used to ensure that the sheet portion is not sucked onto the evacuation port 10 during the evacuation, by applying a force (indicated by arrow 90) to pull the tab 4A away from the evacuation port 10. Many equivalent structures are readily available to the skilled person. For example, a suction may be applied to the outside of sheet portion to pull it away from the evacuation port 10. As noted above, the provision of an internal surface structure on one or both of the sheets 3, 4 may also serve to facilitate proper evacuation of the compartment 6.

There are many conceivable ways to manufacture the packages discussed above. A few different examples will be discussed below in relation to FIGS. 10-13.

Figure 10:
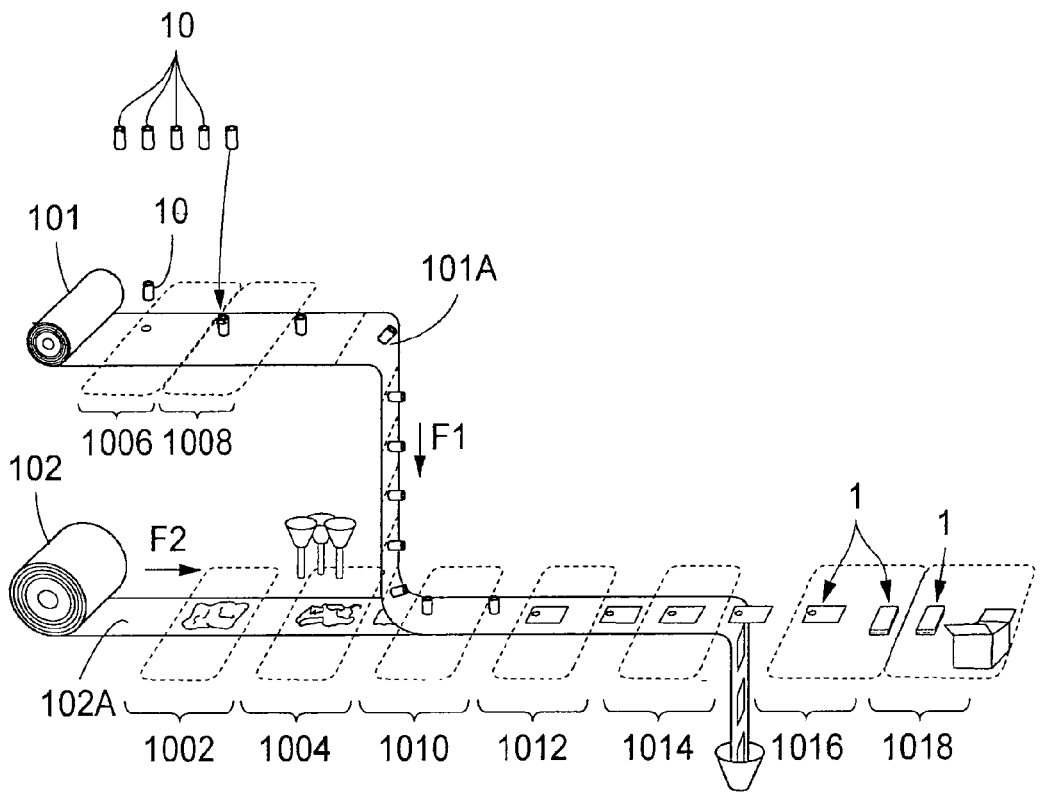
FIG. 10 is a perspective view of a production plant for manufacturing an exemplifying package.

FIG. 10 is a schematic illustration of an exemplifying production plant in which the packages 1 are formed from two rolls 101, 102 of foil and filled with powders in separate trays (cf. FIGS. 1(*d*) and 5). Looking in more detail at the flow of events in the plant of FIG. 10, foils 101A, 102A coming from two rolls (upper foil 101A and lower foil 102A that can be of same or different material) pass a number of processing steps/sites 1002-1018. The feeding directions of the foils 101A, 102A are indicated by arrows F1, F2. In step 1002 in the lower foil track trays are formed in the foil 102A. This may be done by thermoforming, e.g. vacuum forming or pressure forming which are used for manufacture of e.g. blister packages. In step 1004, the different powder groups are measured/weighed and dosed into the preformed trays. At the same time the upper foil 101A is prepared by punching (step 1006) a hole and attaching/welding (step 1008) a connector 10 to the material surrounding the hole. The two foil tracks are then joined together and welded (step 1010) at the periphery to define and seal off the compartment containing the powder groups. Then, in step 1012, the circumference of the package and suspension holes are cut. The processed package is then, in step 1014, exposed to a sub-atmospheric pressure in either a closed environment, e.g. a vacuum chamber, or with a hose attached to the connector, such that air is evacuated from compartment through the connector. Finally, the package 1 is folded (step 1016) and packed (step 1018) into a cardboard box for delivery to customer. When folding, the connector 10 is folded in against the powder side to be protected during transport.

It is currently believed to be an advantage of the production method in FIG. 10 that air (step 1014) is evacuated after the compartment is defined with a final sealing weld (step 1010), since this may make it easier to keep the powder groups in place during manufacture, compared to a production method where the compartment is evacuated before being finally defined in step 1010.

Figure 11:
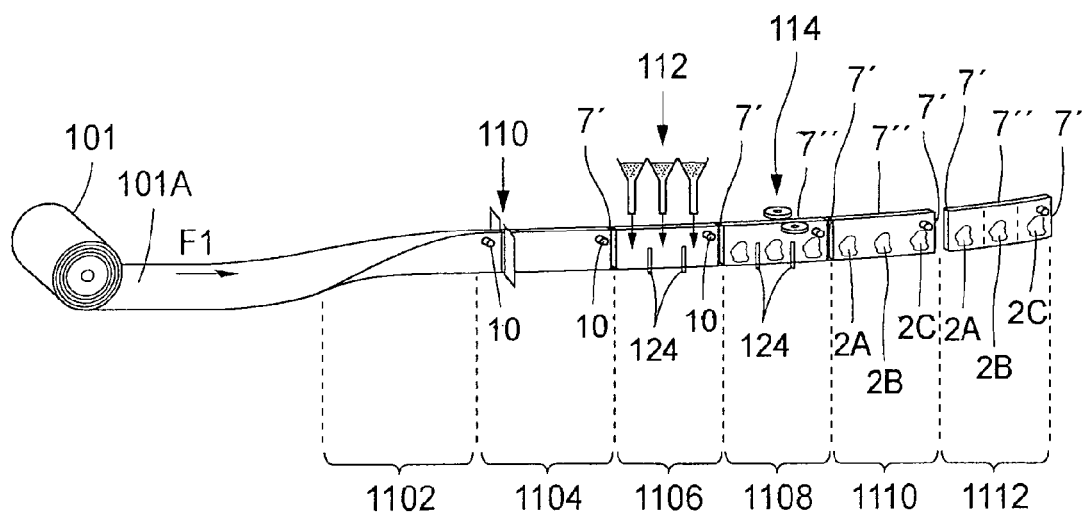
FIG. 11 is a perspective view of an alternative production plant.

FIG. 11 is a schematic illustration of an alternative production plant for manufacturing the packages 1. A foil 101A coming from a roll 101 passes a number of processing steps/sites. The feeding direction of the foil 101A is indicated by arrow F1. In step 1102, the foil 101A is folded along its extent to form two overlapping sheet portions. In step 1104, the compartment is partially defined by means of a welding station 110 which forms a transverse weld line 7' across the overlapping sheet portions, while leaving the upper end portion of the compartment open. Also in step 1104, the connector 10 is attached to one of the sheet portions. In step 1106, temporary pockets are defined in the compartment and the powder groups 2A-2C are carefully metered into the pockets via the open upper end portion, by means of a metering station 112. In step 1108, a weld line 7" is formed in the upper end portion, by means of a welding station 114, to seal the compartment. In step 1108, the compartment is also evacuated, either via the connector 10 after sealing, or before/during sealing by performing steps 1106 and 1108 in a vacuum chamber (not shown). In step 1110, the circumference of the package 1 is cut, and in step 1112 the package 1 is processed for transport, e.g. by folding and packaging.

Figure 12:
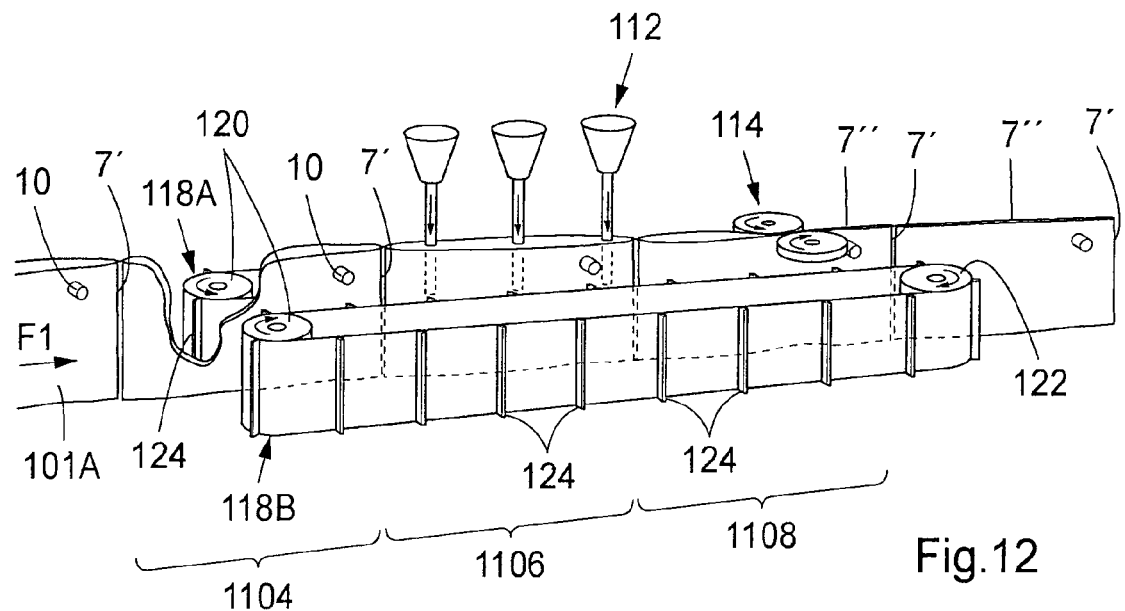
FIG. 12 is a perspective view to illustrate part of FIG. 11 in greater detail.

FIG. 12 is an alternative view of the plant in FIG. 11, to illustrate the step 1106 of defining the temporary pockets in greater detail. As shown, two drive belts 118A, 118B are arranged on opposing sides of the folded foil 101A, where each drive belt 118A, 118B is arranged on two rotatable drive wheels 120, 122 and supports a number of transverse protrusions or fingers 124. The opposing drive belts 118A, 118B are rotated in synchronization such that the fingers 124 are made to abut against each other at a number of locations along the compartment. As shown in FIG. 12, the abutment between the fingers 124 is maintained also during the welding and evacuation step 1108. This will help maintaining the powder groups 2A-2C in position until the opposing sheet portions of the foil 101A have been brought into engagement with the powder groups 2A-2C. In an alternative embodiment (not shown), only one of the drive belts is provided with fingers 124, whereas the other drive belt provides a flat surface to support the folded foil 101A against the pressing action of the fingers 124.

In an alternative (not shown) to the sequence of steps in FIGS. 11-12, step 1108 may be modified to form permanent dividers in the compartment, e.g. by the fingers 124 being exchanged for welding jaws that form weld lines that extend from the closed lower end portion into the compartment to define pockets therein (cf. FIG. 4(a)).

Figure 13:
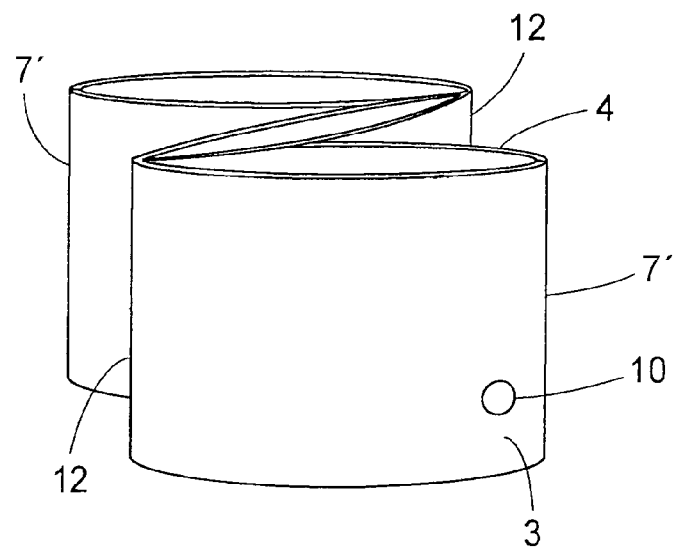
FIG. 13 is a perspective view of an alternative technique for forming a package.

FIG. 13 illustrates yet another alternative way of manufacturing the packages. Here, the compartment is formed with an open end portion, e.g. by combining two foils as in FIG. 10 or by folding a single foil as in FIG. 11. The combined foil material is then folded such that the fold lines 12 define pockets in the compartment, as shown in FIG. 13. Then, the powdery groups are metered into the respective pockets. The compartment is then evacuated, e.g. by sealing the open end portion, unfolding the package and applying a sub-atmospheric pressure via the connector 10, or by sealing the open end portion in a vacuum chamber. It is to be understood that the folding may be carried out on a continuous web of material (e.g. a foil track) or on units that are separated from such a web.

The invention has mainly been described above with reference to a few embodiments. However, as is readily appreciated by a person skilled in the art, other embodiments than the ones disclosed above are equally possible within the scope and spirit of the invention, which is defined and limited only by the appended patent claims.

For example, it is conceivable that two or more of the powder groups that are immobilized in the compartment 6 have identical compositions. Further, the package may include more than one compartment that immobilizes plural powder groups and/or the package 1 may include one or more further compartments, of any type, that contains one powder group each. Optionally, the compartments of the package may be separated using conventional dividers that are ruptured either manually or automatically, e.g. by application of fluid pressure.

It is also possible that the mixing with the solvent only partially takes place within the compartment, e.g. by the solvent being repeatedly circulated into and out of the compartment. The compartment may comprise an inlet connector and an outlet connector, such that the solvent can be driven to flow through the compartment, where the solvent may be continuously driven to flow through the compartment, possibly using re-circulation, until the powdery material is dissolved. Alternatively, the solvent is admitted via the inlet connector to mix with and dissolve the powdery material, whereupon the prepared medical solution is expelled via the outlet connector.

In another embodiment, the mixing and dissolution of the powdery material takes place exclusively outside of the compartment. For example, the powder groups may be poured or sucked out of the compartment to be mixed with the solvent. In such an embodiment, the connector may be omitted from the package. It is also conceivable that the mixing with the solvent takes place in a separate compartment within the package.

It is also conceivable to use the concept of establishing a sub-atmospheric pressure in a compartment that holds a single powder group, or plural powder groups that all have the same composition. It is currently believed that provision of a sub-atmospheric pressure or "vacuum" in the compartment serves to significantly improve the shelf life of the powdery material, especially for substances that are degraded by the presence of moisture. Generally, such a package for storing a powdery material comprises a compartment and powdery material in the compartment, with a sub-atmospheric pressure being established within the compartment. Like in the above-described embodiments, it may be preferable that the opposing wall portions of the compartment are brought and/or held into engagement with the powdery material, e.g. by the action of the sub-atmospheric pressure. Likewise, it may be desirable that the package comprises a connector for selectively admitting a fluid into the package for expanding the compartment and enabling mixing of the powdery material with the solvent as part of a process for preparing a medical solution.

The invention claimed is:

1. A package for storing powdery material which is to be mixed with a solvent to form a medical solution, said package comprising:
    a compartment which is at least partially defined by two opposing wall portions and contains the powdery material in the form of at least two distinct sets of powdery material of different compositions, wherein the opposing wall portions are brought into engagement with the powdery material so as to immobilize the sets of powdery material, and the at least two distinct sets of powdery material are separated from each other by a constriction region, in which the wall portions are brought into close proximity with each other without being fixedly attached to each other; and
    a connector configured to selectively admit a fluid into the package, wherein the admitted fluid expands the compartment and mixes the sets of the powdery material with the solvent in the expanded compartment.

2. The package of claim 1, wherein at least one of the opposing wall portions is deformed into said engagement.

3. The package of claim 1, wherein at least one of the opposing wall portions is made of flexible material.

4. The package of claim 1, wherein the opposing wall portions are brought into said engagement by evacuation of gas from the compartment.

5. The package of claim 4, wherein the compartment is at a sub-atmospheric pressure.

6. The package of claim 4, wherein the compartment is evacuated such that the powdery material is at least partially compacted.

7. The package of claim 1, wherein the spacing of the opposing wall portions in the constriction region is less than an effective minimum diameter of the powdery material.

8. The package of claim 1, including a fold or bending in the constriction region.

9. The package of claim 1, further comprising a reduced adhesion region between the wall portions in the constriction region.

10. The package of claim 9, wherein said reduced adhesion region comprises a three-dimensional surface pattern on at least one of the wall portions.

11. The package of claim 10, wherein the surface pattern has a depth of less than 50 μm.

12. The package of claim 10, wherein the surface pattern is defined by elongate ridges that extend perpendicularly to a direction of separation between the spaced sets.

13. The package of claim 9, wherein said reduced adhesion region comprises a respective composition of the wall portions having low mutual adhesion.

14. The package of claim 1, wherein at least one of the sets of the powdery material is arranged in a pocket inside the compartment.

15. The package of claim 14, wherein the pocket is at least partially defined by an internal partition extending into the compartment from a closed perimeter portion of the compartment.

16. The package of claim 14, wherein the pocket is at least partially defined by an internal corner portion at a perimeter of the compartment.

17. The package of claim 14, wherein the pocket is formed as a tray-shaped deformation in one of said opposing wall portions.

18. The package of claim 1, further comprising a check valve in fluid communication with the compartment.

19. The package of claim 18, wherein the check valve is integrated with the connector.

20. The package of claim 1, wherein said fluid is one of a gas and said solvent.

21. The package of claim 1 wherein the medical solution is one of a dialysis concentrate, a dialysis solution, an infusion solution, a nutrition solution, a replacement solution, and a plasma expander solution.

22. A method of manufacturing a package for storing powdery material which is to be mixed with a solvent to form a medical solution, said method comprising:
    arranging the powdery material in a compartment which is at least partially defined by two opposing wall portions, wherein the powdery material is arranged in the form of at least two distinct sets of powdery material of different compositions, the at least two distinct sets of powdery material being separated from each other by a constriction region;
    providing a connector for selectively admitting a fluid into the package to expand the compartment and enable mixing of the sets of the powdery material with the solvent in the compartment to prepare the medical solution; and
    bringing the opposing wall portions into engagement with the powdery material to immobilize the sets of the powdery material, wherein the wall portions are brought into close proximity with each other in the constriction region without being fixedly attached to each other.

23. A method of preparing a medical solution, said method comprising:
    obtaining a package comprising a compartment and a connector, the compartment at least partially defined by opposing wall portions and containing powdery material in the form of at least two distinct sets of powdery material of different compositions, wherein the opposing wall portions are brought into engagement with the powdery material so as to immobilize the sets of powdery material, and the at least two distinct sets of powdery material are separated from each other by a constriction region, in which the wall portions are brought into close proximity with each other without being fixedly attached to each other;
    connecting the connector to a source of a solvent; and
    selectively admitting the solvent into the package via the connector, whereby the compartment is expanded and the solvent mixes with the sets of the powdery material inside the compartment as part of a process to prepare the medical solution.

24. The method of claim 23 further comprising using the prepared medical solution in a peritoneal dialysis treatment.

25. The method of claim 23 further comprising using the prepared medical solution in a blood dialysis treatment.

26. A package comprising:
    opposing and overlapping walls at least one of which is deformable, wherein the walls have a collapsed configuration and an expanded configuration;
    a first pile of a first powdery material and a second pile of a second powdery material wherein each pile is immobilized between the walls when in the collapsed configuration such that the first pile is separated from the second pile, and the first and second piles are separated from each other by a constriction region, in which the walls are brought into close proximity with each other without being fixedly attached to each other; and
    a connector establishing a fluid passage from an external fluid source to an area between the walls,
    wherein at least one of the walls expands to the expanded configuration as fluid from the fluid source enters through the connector, and the first pile and second pile mix with the fluid to form a medical solution contained by the walls.

27. The package of claim 26 wherein a pressure between the walls in the collapsed configuration is sub-atmospheric.

28. The package of claim 26 wherein a fold in the walls is between the first and second sheets.

29. The package of claim 26 wherein a three-dimensional surface pattern on at least one of the walls abuts the opposing wall in a region between the first and second piles.

30. The package of claim 29 wherein the surface pattern has a depth of less than 50 μm.

31. The package of claim 29 wherein the surface pattern is defined by elongated ridges extending transversely to a line between the first and second piles.

32. A method comprising: storing a first powdery material in a first region of a package and a second powdery material in a second region of the package, wherein the package includes at least one deformable wall overlapping the first and second powdery materials, wherein the deformable wall separates the first and second powdery materials, and wherein the first and second regions are separated from each other by a constriction re ion, in which the deformable wall is brought into close proximity with an opposing wall without being fixedly attached to the opposing wall;
    injecting a fluid into the package;
    expanding the deformable wall with the injected fluid to form a compartment in the package which includes the first powdery material and the second powdery material, and
    mixing the fluid with the first powdery material and the second powdery material to form a medical solution including the first and second powdery materials in the solution.

33. The method of claim 32 wherein prior to storing the first powdery material and the second powdery material the at least one deformable wall is collapsed onto the first and second powdery materials.

34. The method of claim 33 wherein the at least one deformable material is collapsed by evacuating air from the package.

35. The method of claim 32 wherein the injection of the fluid occurs proximate to a time at which the medical solution is discharged from the package.

36. The method of claim 32 wherein the fluid is a blood treatment liquid.

37. The method of claim 32 further comprising discharging the solution for use in a peritoneal dialysis treatment or an extracorporeal treatment of blood.

* * * * *